United States Patent [19]

Hallgren

[11] 4,349,485

[45] Sep. 14, 1982

[54] CATALYTIC AROMATIC CARBONATE PROCESS USING MANGANESE TETRADENTATE REDOX CO-CATALYSTS

[75] Inventor: John E. Hallgren, Scotia, N.Y.

[73] Assignee: General Electric Company, Schenectady, N.Y.

[21] Appl. No.: 97,431

[22] Filed: Nov. 23, 1979

[51] Int. Cl.³ .............................................. C07C 68/04
[52] U.S. Cl. ................................ 260/463; 260/429 H
[58] Field of Search ............................ 260/463, 429 H

[56] References Cited

U.S. PATENT DOCUMENTS

| | | | |
|---|---|---|---|
| 2,556,316 | 6/1951 | Cartledge | 260/429 H |
| 2,926,184 | 2/1960 | Irish et al. | 260/429 H |
| 3,053,804 | 9/1962 | Caldwell et al. | 260/429 H |
| 4,096,168 | 6/1978 | Hallgren | 260/463 |
| 4,096,169 | 6/1978 | Chalk | 260/463 |

*Primary Examiner*—Donald G. Daus
*Assistant Examiner*—M. C. Eakin
*Attorney, Agent, or Firm*—Peter A. Bielinski; James C. Davis, Jr.; Joseph T. Cohen

[57] ABSTRACT

An enhanced catalytic aromatic carbonate process which comprises contacting a phenol, carbon monoxide, an oxidant, a base, the Group VIIIB element selected from ruthenium, rhodium, palladium, osmium, iridium or platinum, and a manganese tetradentate redox co-catalyst. The resulting aromatic mono- and/or poly-carbonates are useful in the preparation of polycarbonates or as polycarbonates per se, respectively, which can be molded or formed into films, sheets, fibers, laminates or reinforced plastics by conventional techniques.

22 Claims, 1 Drawing Figure

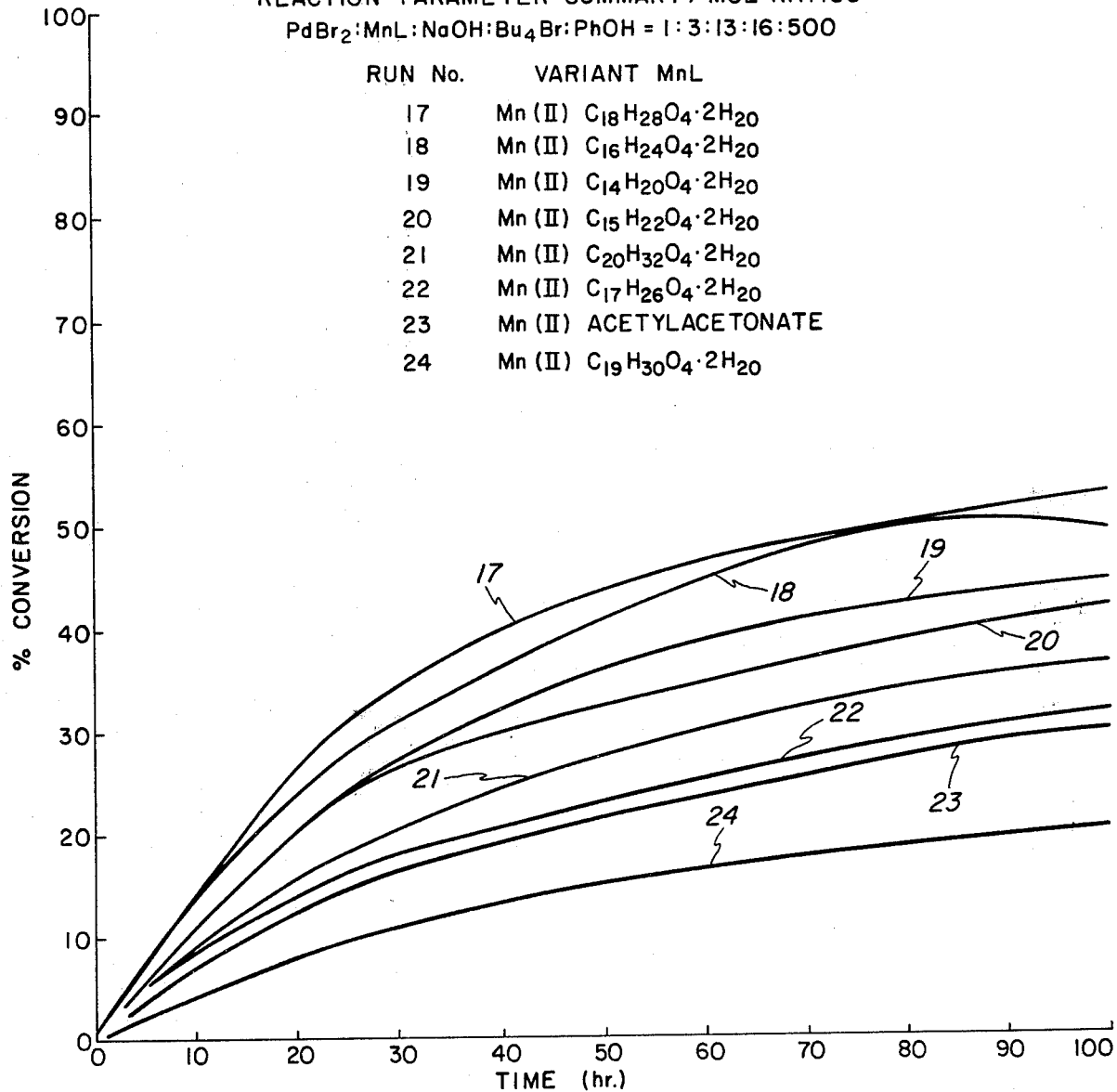

CATALYTIC AROMATIC CARBONATE PROCESS USING MANGANESE TETRADENTATE REDOX CO-CATALYSTS

CROSS-REFERENCE TO RELATED APPLICATIONS

This invention is related to my U.S. patent applications Ser. No. 834,534 filed Sept. 19, 1977 (a continuation of Ser. No. 731,443 filed Oct. 12, 1976, now abandoned) now U.S. Pat. No. 4,221,920 issued Sept. 9, 1980; Ser. No. 731,493 filed Oct. 12, 1976, now U.S. Pat. No. 4,096,168 issued June 20, 1978; Ser. No. 892,509 filed Apr. 3, 1978, now U.S. Pat. No. 4,201,721 issued May 6, 1980; Ser. No. 037,636 filed May 11, 1979, now U.S. Pat. No. 4,260,802; Ser. No. 038,907 filed May 14, 1979, now abandoned; and A. J. Chalk's U.S. patent application Ser. No. 892,497 filed Apr. 3, 1978 (a continuation-in-part of Ser. No. 731,493 filed Oct. 12, 1976, now U.S. Pat. No. 4,096,169 issued June 20, 1978) now U.S. Pat. No. 4,187,242 issued Feb. 5, 1980; Ser. No. 731,495, also filed Oct. 12, 1976, now abandoned. All of the aforesaid applications are assigned to the same assignee as the assignee of this application.

BACKGROUND OF THE INVENTION

1. Field of the Invention

This invention relates to an enhanced catalytic aromatic carbonate process which comprises contacting a phenol, carbon monoxide, an oxidant, a base, the Group VIIIB element selected from ruthenium, rhodium, palladium, osmium, iridium or platinum and a manganese tetradentate redox co-catalyst.

2. Description of the Prior Art

As broadly disclosed in my Catalytic Aromatic Carbonate Process patent application referenced above U.S. Pat. No. 4,201,821 issued May 6, 1980—aromatic carbonates can be prepared by contacting a phenol, carbon monoxide, an oxidant, a base, the Group VIIIB element selected from ruthenium, rhodium, palladium, osmium, iridium, or platinum, and a manganese redox co-catalyst.

Unexpectedly, I have found that optimum aromatic carbonate process yields result when a certain class of manganese tetradentate redox co-catalysts are employed in my and Chalk's catalytic aromatic carbonate processes.

DESCRIPTION OF THE INVENTION

This invention embodies an enhanced catalytic aromatic carbonate process which comprises contacting a phenol, carbon monoxide, an oxidant, a base, the Group VIIIB element selected from ruthenium, rhodium, palladium, osmium, iridium or platinum, and a manganese tetradentate redox co-catalyst.

Any of the phenols, solvents, bases, the Group VIIIB elements, oxidants, or reaction parameters relative to amounts, time, temperature and pressure disclosed in Chalk U.S. Pat. No. 4,187,242 issued Feb. 5, 1980; and Hallgren U.S. Pat. No. 4,221,920 issued Sept. 9, 1980; U.S. Pat. No. 4,096,168 issued June 20, 1978, U.S. Pat. No. 4,201,721 issued May 6, 1980, U.S. Pat. No. 4,260,802 issued Apr. 7, 1981, and U.S. Pat. No. 4,096,169 issued June 20, 1978 all assigned to the same assignee as the present invention, can be employed in my process. Accordingly, their descriptions are hereby incorporated herein the their entirety by reference. More particularly, phenols which can be employed in the present invention are disclosed in Chalk U.S. Pat. No. 4,187,242 issued Feb. 5, 1980 at col. 2, line 58—col. 3, line 38. Solvents which can be used in the present invention are disclosed in Chalk above at col. 4, line 62—col. 5, line 7. Bases which can be used in the present invention include those disclosed in Chalk above at col. 5, line 8—col. 5, line 34. Group VIIIB elements useful in the present invention are disclosed in Chalk at col. 3, line 39—col. 4, line 61. Oxidants useful in the invention are disclosed in Chalk above at col. 5, line 35—col. 5, line 65. Reaction parameters which can be employed in the present invention are disclosed in Chalk at col. 6, line 26—col. 7, line 18. As used herein and in the appended claims the expression "catalytic aromatic process" includes all reactions wherein carbonates and/or salicylates are formed as a result of the existence of a reaction environment which contains in addition to certain manganese tetradentate redox co-catalysts a phenol, a base, the Group VIIIB element and an oxidant.

The reaction parameter essential to the enhanced process of my invention comprises the use of a manganese complex containing a tetradentate ligand "L" having at least two β-diketone groups within a single ligand skeletal backbone subject to the proviso that at least two separate β-diketone carbonyl groups of the ligand are separated from each other by 6 to 12 substantially linear carbon atoms.

Illustratively, the tetradentate ligands can be described by a ligand "L" of the generic formula:

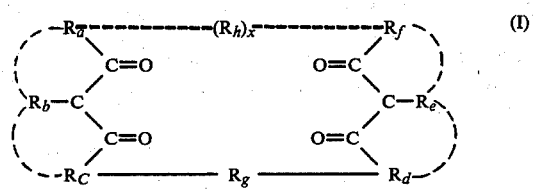

wherein independently $R_a$, $R_b$, $R_c$, $R_d$, $R_e$ and $R_f$ are the same, different or conjoint acyclic or cyclic hydrocarbon radicals, optionally $R_b$ and $R_e$ are hydrogen, subject to the proviso that at least one of $R_g$ or $R_h$ is a divalent hydrocarbon radical, further wherein $R_g$ and $R_h$ are the same or different hydrocarbon radicals, the sum of the linear carbon atoms of $R_c + R_g + R_d$ is from 6 to 12, preferably 4 to 10, the sum of the linear carbon atoms of $R_a + R_h + R_f$ is from 6 to 12, preferably 4 to 10, and x is an integer of 0 or 1.

The tetradentate ligands can be prepared by any method known to those skilled in the art including two-fold terminal alkylation of disodio β-diketones with methylene halides to form bis-β-diketones in accord with the techniques of K. G. Hampton, R. J. Light, and C. R. Hauser, published in the Journal of Organic Chemistry 30, 1413–1416 (May 1965). Illustratively, the reactions involve contacting β-diketones with sodamide in liquid ammonia, and subsequently alkylating the terminal positions of the β-diketones with an alkylene α,ω-dihalides to form bis-β-diketones. Those of ordinary skill in the art, by selecting the appropriate β-diketone and alkylene α,ω-dihalide can prepare tetradentate ligands having the appropriate carbon length which meets the proviso of the linear carbon length limitations set out hereinbefore with respect to combinations of the $R_c + R_g + R_d$ group and the $R_a + R_h + R_f$ groups.

The manganese tetradentates can be prepared by introducing manganese ion(s) having any oxidation state, e.g. from −1 to +7, to a tetradentate ligand of the genus described in Formula I. The manganese tetradentates are readily formed by contacting tetradentates of Formula I in an aqueous basic solution with a soluble form of manganese, e.g. manganese salts in the form of halides, nitrates, sulfates, oxalates, acetates, carbonates, propionates, hydroxides, tartrates, etc. Any base can be used, e.g. alkali or alkaline earth metal bases including sodium hydroxide, potassium hydroxide, as well as other alkaline and alkaline earth metal hydroxides, carbonates, etc.

For purposes of clarity, "manganese tetradentates" are defined herein and in the appended claims as the molecular structure which arises from the union of a manganese atom with at least four donor atoms of the bis-β-diketone ligand of Formula I above. This association can be described as $(L)_x Mn$ wherein L is a ligand of Formula I, Mn is the transition metal manganese, x is a positive integer at least equal to about 1.0. In my process mixtures containing manganese exhibiting various oxidation states—also containing various species of the tetradentate ligand genus described by Formula I—can be employed. Presently, preferably, the oxidation state of the starting manganese tetradentate reactant is divalent Mn(II) or $Mn^{++}$.

The following examples illustrate the best mode of practicing this invention.

EXAMPLE I

Preparation of pentadecane-2,4,12,14-tetraone ($C_{15}H_{24}O_4$)

A 1-l three-neck flask—equipped with an inlet tube, overhead mechanical stirrer, and dry-ice reflux condensor—was cooled with dry-ace/acetone to −78° C., and charged with 400 ml of anhydrous ammonia ($NH_3$), 10.2 g (0.44 mol) of sodium metal (Na) and a trace of ferric chloride ($FeCl_3$). The mixture was stirred until the Na dissolved and a dark blue color discharged. 22.4 g (0.22 mol) of acetylacetone was added via a syringe to the resulting sodium amide solution. The mixture was stirred for ca. 30 minutes at −78° C. at which time complete solution occurred. 23.0 g (0.10 mol) of 1,5-dibromopentane dissolved in 50 ml of ether via a 125 ml pressure equalizing addition funnel was added dropwise to the reaction mixture over a 20 minute period and then refluxed for one hour. An additional 400 ml of ether was added and the ammonia was allowed to boil off. 200 ml of water and 60 ml concentrated hydrochloric acid was then added to the resulting slurry. The etherical layer was separated and contacted with an additional 50 ml of concentrated HCl. The aqueous layer was extracted 3 times with 300 ml portions of ether, dried over sodium sulfate and filtered. The ether layer was removed under reduced pressure to yield a white solid which was recrystallized from methanol to provide 18.27 g (68%) of the title compound having a mp of 73°–74° C. of the formula

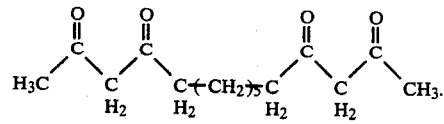

The pentadecane-2,4,12,14-tetraone was further characterized and identified using MS, $H^1$ nmr, $C^{13}$ nmr, ir, and combustion analysis techniques.

A resume describing the empirical formula of the α,ω-dihaloalkane and the empirical formula, melting point, % yield, % C, and % H analyzed and calculated for the bis(β-diketone) is set out in Table 1:

TABLE 1

| Run No. | Dihalide | Bis(β-diketone) | mp | % Yield | % C (cal'd) | % H (calc'd) |
|---|---|---|---|---|---|---|
| 1 | n-1,5-$C_5H_{10}Br_2$ | $C_{15}H_{24}O_4$ | 73–74° | 68 | 67.4 (67.2) | 9.0 (9.0) |

EXAMPLES 2–7

Preparation of other bis(β-diketones)

A series of $C_{14}$ and $C_{16}$ to $C_{20}$ bis(β-diketones) were prepared in accord with the general procedure described in Example 1. A resume of the α,ω-dihaloalkane reactants and the resulting bis(β-diketones) is set out in Table 2:

TABLE 2

| Run No. | Dihalide | Bis(β-diketone) | mp | % Yield | % C (calc'd) | % H (calc'd) |
|---|---|---|---|---|---|---|
| 2 | n-1,4-$C_4H_8Br_2$ | $C_{14}H_{22}O_4$ | 72–73° | 71 | 65.7 (66.1) | 9.0 (8.7) |
| 3 | n-1,6-$C_6H_{12}Br_2$ | $C_{16}H_{26}O_4$ | 75–76° | 68 | 67.9 (68.0) | 9.5 (9.2) |
| 4 | n-1,7-$C_7H_{14}Br_2$ | $C_{17}H_{28}O_4$ | 82–84° | 37 | 68.6 (68.9) | 9.6 (9.5) |
| 5 | n-1,8-$C_8H_{16}Br_2$ | $C_{18}H_{30}O_4$ | 84–85.5° | 40 | 69.7 (69.6) | 9.7 (9.7) |
| 6 | n-1,9-$C_9H_{18}Br_2$ | $C_{19}H_{32}O_4$ | 87° | 53 | 70.0 (70.4) | 9.9 (9.9) |
| 7 | N-1,10-$C_{10}H_{20}Br_2$ | $C_{20}H_{34}O_4$ | 92–93° | 62 | 70.8 (71.0) | 10.1 (10.1) |

Preparation of Manganese (II) Tetradentate of the Empirical Formula Mn(II)$C_{18}H_{28}O_4$ A 125 ml meyer flask equipped with a magnetic spin bar was charged with 0.93 g (3.0 mmol) of octadecane-2,4,15,17-tetraone, abbreviated $C_{18}H_{30}O_4$, 0.48 g (6.0 mmol) of 50% aqueous caustic and 70 ml of water in a nitrogen box. The resulting mixture was warmed to boiling and combined with a solution of 0.735 g (3.0 mmol) of manganese diacetate tetrahydrate, abbreviated Mn(OAc)$_2$.4H$_2$O which had been previously dissolved in 40 ml of hot water. Immediately a white precipitate formed. The mixture was boiled for ca. 5 minutes to obtain larger crystals, suction filtered, water washed, methanol washed, dried in vacuo at 70° C. overnight to yield 1.02 g (85%) of an off white powder of the title compound having a mp of 110–115 of the empirical formula Mn($C_{18}H_{30}O_4$)H$_2$O. The Mn(II) tetradentate was further characterized and identified by field desorption-MS and elemental analysis.

A resume of the melting point, % yield, and % Mn found vs. Mn calculated is set out in Table 3:

TABLE 3

| Run No. | Mn(II)bis(β-diketone) | mp | % Yield | % Mn (calc'd) |
|---|---|---|---|---|
| 8 | Mn(II)C$_{18}$H$_{28}$O$_4$ | 110–115 | 86 | 14.0 (14.4) |

EXAMPLES 9–15

Preparation of a series of Mn(II)bis(β-diketones)

A series of C$_{14-20}$ Mn(II) bis(β-diketones) were prepared in accord with the general procedure described in Example 8. A resume of resulting manganese tetradentates is set out in Table 4:

TABLE 4

| Run No. | Mn(II)bis(β-diketone) | mp | % Yield | % Mn (calc'd) |
|---|---|---|---|---|
| 9  | Mn(II)C$_{14}$H$_{20}$O$_4$ | 98–101  | 31 | 17.1 (16.9) |
| 10 | Mn(II)C$_{15}$H$_{22}$O$_4$ | 102–105 | 94 | 16.1 (16.2) |
| 11 | Mn(II)C$_{16}$H$_{24}$O$_4$ | 105–108 | 90 | 15.9 (15.6) |
| 12 | Mn(II)C$_{17}$H$_{26}$O$_4$ | 107–110 | 98 | 15.1 (15.0) |
| 13 | Mn(II)C$_{18}$H$_{28}$O$_4$ | 110–115 | 86 | 14.0 (14.4) |
| 14 | Mn(II)C$_{19}$H$_{30}$O$_4$ | 110–115 | 71 | 14.0 (13.9) |
| 15 | Mn(II)C$_{20}$H$_{32}$O$_4$ | 113–117 | 73 | 13.7 (13.4) |

EXAMPLE 16

Preparation of diphenyl carbonate using Mn(II) C$_{18}$ bis(β-diketones)

A 100 ml 3-neck flask equipped with subsurface carbon monoxide and air inlets, a gas exit tube, and a magnetic spin bar was charged with 4.7 g (0.050 mol) of phenol, 10 g of 3A molecular sieves—Linde(TM) Type 3A activated by heating to 200° C. in vacuo for 72 hours, stored until use under nitrogen in a dry container, 0.52 g (1.6 mmol) of tetrabutylammonium bromide, 0.104 g (1.3 mmol) of 50% aqueous caustic, 0.100 g of bibenzyl as an internal standard, and 40 ml of methylene chloride. The resulting mixture was stirred at room temperature for 90 minutes, 0.114 g (0.3 mmol) of Mn(II)C$_{18}$H$_{30}$O$_4$, 0.025 g (0.1 mmol) of palladium bromide (PdBr$_2$) were added, and then carbon monoxide (0.01 SCFH) and air (0.03 SCFH) were bubbled slowly through the reaction mixture. Aliquots were withdrawn periodically, filtered through a 0.5µ teflon filter and analyzed by LC.

The rate of carbonylation is illustrated in FIG. 1, Run No. 17, which summarizes the percent diphenyl carbonate formed versus reaction time for the Mn(II)C$_{18}$ bis(β-diketone) redox co-catalyst.

EXAMPLES 17–23

Preparation of diphenyl carbonates using Mn(II) C$_{14-17}$ and C$_{19-20}$ bis(β-diketones) and Mn(II) bis(acetylacetonate)

A series of carbonylation reactions were carried out in accord with the general procedure describes in Example 16 with the only variable being the type of manganese tetradentate used in the process. The rate of carbonylation is illustrated in FIG. 1, Run Nos. 18–24, which summarize the percent diphenyl carbonate formed versus reaction time for the Mn(II)C$_{14-17}$ and C$_{19-20}$ bis(β-diketone) redox co-catalysts.

Analogous enhanced redox co-catalyst benefits can be obtained wherein the manganese tetradentate redox co-catalysts described herein are employed in conjunction with an aromatic polyphenol reactant, e.g. bis(4-hydroxyphenyl)propane 2,2, carbon monoxide, an oxidant, a base and a Group VIIIB element selected from ruthenium, rhodium, palladium, osmium, iridium or platinum in the formation of aromatic polycarbonates.

I claim:

1. An aromatic carbonate process wherein an aromatic phenol of the formulas

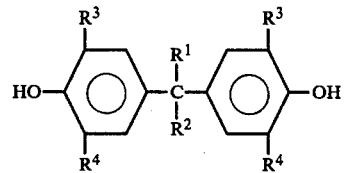

or

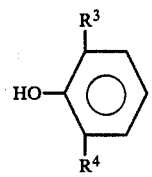

wherein independently each $R^1$ and $R^2$ is hydrogen, $C_{1-4}$ alkyl or phenyl and independently each $R^3$ and $R^4$ is hydrogen or $C_{1-4}$ alkyl, carbon monoxide, a base, a Group VIIB element selected from ruthenium, rhodium, palladium, osmium, iridium or platinum, and an oxidant having an oxidation potential greater than that of the said selected Group VIIIB element are contacted, the improvement comprising the use of a redox co-catalyst selected from manganese tetradentates of the formula (L)$_x$Mn wherein L is a C$_{14-20}$H$_{22-34}$O$_4$ bis(β-diketone), Mn is the transition metal manganese, and x is a positive integer at least equal to about 1.0.

2. The claim 1 process wherein L is a C$_{18}$H$_{30}$O$_4$ bis(β-diketone).

3. The claim 1 process, wherein said Group VIIIB element is present in an ionic form.

4. The claim 1 process, wherein said base is a tertiary amine.

5. The claim 1 process, wherein said Group VIIIB element is associated with a carbonyl group.

6. The claim 1 process, wherein said Group VIIIB element is associated with a halide.

7. The claim 1 process, wherein said Group VIIIB element is coordinated with a ligand selected from an arsine, a stilbene, a phosphine, a nitrile or a halide.

8. The claim 1 process, wherein said Group VIIIB element is associated with an inorganic halide compound.

9. The claim 1 process, further comprising separating at least a portion of the resulting aromatic carbonate product.

10. The claim 1 process, further comprising substantially anhydrous reaction conditions.

11. The claim 1 process further comprising the use of a drying agent.

12. The claim 1 process, further comprising the use of a molecular sieve drying agent.

13. The claim 1 process further comprising the use of a phase transfer agent.

14. The claim 1 process further comprising the use of a molecular sieve and phase transfer agent.

15. The claim 14 process, wherein the base is an alkali or alkaline earth metal base, the oxidant is air, the Group VIIIB element is a form of palladium and the phase transfer agent is an onium halide.

16. The claim 15 process, wherein the Group VIIIB element is a palladium halide.

17. The claim 16 process, wherein the phenol is of the formula

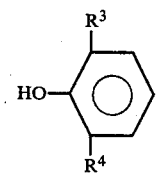

wherein each $R^3$ and $R^4$ are hydrogen, the base is sodium hydroxide, the oxidant is air, the Group VIIIB element is palladium(II)dibromide, and the phase transfer agent is tetrabutylammonium bromide.

18. The claim 1 process wherein L is a $C_{16}H_{26}O_4$ bis($\beta$-diketone).

19. The claim 1 process wherein L is a $C_{14}H_{22}O_4$ bis($\beta$-diketone).

20. The claim 1 process wherein L is a $C_{15}H_{24}O_4$ bis($\beta$-diketone.

21. The claim 1 process wherein L is a $C_{20}H_{34}O_4$ bis($\beta$-diketone).

22. The claim 1 process wherein the aromatic phenol is of the formula:

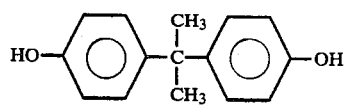

* * * * *